United States Patent
Lemmens et al.

(10) Patent No.: US 6,479,525 B2
(45) Date of Patent: Nov. 12, 2002

(54) ASPARTATE DERIVATIVE OF AMLODIPINE

(75) Inventors: Jacobus M. Lemmens, Mook; Theodorus H. A. Peters, Arnhem; Franciscus B. G. Benneker, Rheden, all of (NL)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 09/938,817

(22) Filed: Aug. 27, 2001

(65) Prior Publication Data

US 2002/0128296 A1 Sep. 12, 2002

Related U.S. Application Data

(63) Continuation-in-part of application No. 09/809,349, filed on Mar. 16, 2001, now abandoned.
(60) Provisional application No. 60/258,602, filed on Dec. 29, 2000.

(51) Int. Cl.$^7$ .................... C07D 211/90; A61K 31/455
(52) U.S. Cl. ....................... 514/356; 546/321
(58) Field of Search ................... 514/356; 546/321

(56) References Cited

U.S. PATENT DOCUMENTS

| | | | |
|---|---|---|---|
| 4,572,909 A | * 2/1986 | Campbell et al. ........... 514/356 |
| 4,879,303 A | 11/1989 | Davison et al. |
| 4,983,740 A | 1/1991 | Peglion et al. |
| 5,155,120 A | 10/1992 | Lazar et al. |
| 5,389,654 A | 2/1995 | Furlan et al. |
| 5,438,145 A | 8/1995 | Furlan et al. |
| 6,046,337 A | 4/2000 | Bozsing et al. |

FOREIGN PATENT DOCUMENTS

| EP | 0 089 167 B1 | 10/1986 |
| EP | 0 244 944 | 1/1990 |
| EP | 0 290 211 B1 | 9/1991 |
| EP | 0 534 520 B1 | 3/1997 |
| EP | 0 902 016 A1 | 3/1999 |
| EP | 0 963 980 A2 | 12/1999 |
| WO | 99/25688 | 5/1999 |
| WO | 99/52873 | 10/1999 |
| WO | 00/24714 | 5/2000 |
| WO | 00/35873 | 6/2000 |
| WO | 00/35910 | 6/2000 |

OTHER PUBLICATIONS

Alker et al., "Long–acting dihydropyridine calcium antagonists. 9. Structure activity relationships around amlodipine", Eur J Med Chem (1991) 26, 907–913.
Amlodipine Besylate Monograph, Pharmaeuropa vol. 10, No. 2, 197–198, Jun. 1998.
Faulkner et al., "Absorption of Amlodipine Unaffected by Food", Arzneim Forsch/Drug Res. 39 (11), No. 7, (1989).
McDaid and Deasy, "Formulation development of a transdermal drug delivery system for amlodipine base", International Journal of Pharmaceutics 133 (1996) 71–83.
Arrowsmith et al., "Long–Acting Dihydropyridine Calcium Antagonists. 1. 2–Alkoxymethyl Derivatives Incorporating Basic Substituents", J. Med. Chem. American Chemical Society, 1986, 29, 1696–1702.
FDA FOIA Material on Amlodipine Besylate, NDA No. 19–787, "Review of an Original NDA", Oct. 10, 1990.

\* cited by examiner

*Primary Examiner*—Frederick Krass
(74) *Attorney, Agent, or Firm*—Fleshner & Kim, LLP

(57) ABSTRACT

An amlodipine derivative having the following formula is useful, either alone or in combination with amlodipine, as a pharmaceutical in treating angina and hypertension.

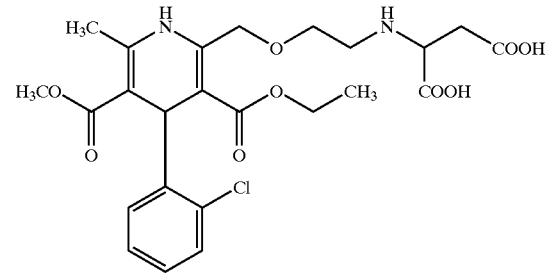

23 Claims, 2 Drawing Sheets

ASPARTATE DERIVATIVE OF AMLODIPINE

This application claims the benefit of priority under 35 U.S.C. §120 from prior co-pending U.S. patent application Ser. No. 09/809,349, filed Mar. 16, 2001, now abandoned, the entire contents of which are incorporated herein by reference. Further, this application claims the benefit of priority under 35 U.S.C. §119(e) from provisional patent application Serial No. 60/258,602, filed Dec. 29, 2000, the entire contents of which are incorporated herein by reference.

BACKGROUND OF THE INVENTION

1. Field of the Invention

The present invention relates to a novel compound, to processes for preparing it and to its use in treating medical disorders. In particular the present invention relates to a novel derivative of Amlodipine.

2. Description of the Related Arts

Calcium channel blockers (calcium antagonists) are useful in treating cardiac conditions including angina and/or hypertension. Dicarboxylate-dihydropyridine derivatives are generally known to possess calcium channel blocking activity. For example, EP 089 167 and corresponding U.S. Pat. No. 4,572,909 disclose a class of 2-amino group-3,5-dicarboxylate dihydropyridine derivatives as being useful calcium channel blockers. These patents identify that one of the most preferred compounds is 2-[(2-aminoethoxy)methyl]-4-(2-chlorophenyl)-3-ethoxycarbonyl-5-methoxycarbonyl-6-methyl-1,4-dihydropyridine. This compound, which is now commonly known as amlodipine, has the following formula:

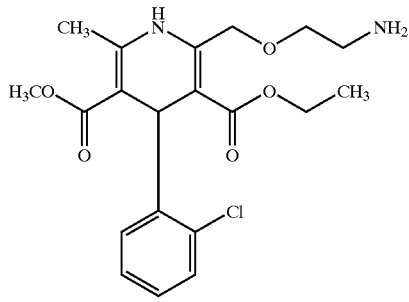

Amlodipine exhibits good bioavailability and has a long half-life in the body. While a variety of acid addition salts are taught in these patents to be suitable, the maleate salt is identified as the most preferred acid addition salt. However, the commercial product of amlodipine (NORVASC by Pfizer) uses amlodipine besylate (benzene sulfonate) and not amlodipine maleate. Indeed, subsequent patents EP 244 944 and corresponding U.S. Pat. No. 4,879,303 indicate that the besylate salt provides certain advantages over the known salts including good formulating properties. Apparently, amlodipine maleate suffered from tabletting and stability problems so as to cause a switch during development to the besylate salt. (See "Review of Original NDA" for NDA# 19-787 of 10.10.1990, obtainable from FDA under Freedom of Information Act). The stability and tabletting issues/causes are not publicly disclosed in the information available from the FDA.

SUMMARY OF THE INVENTION

The present invention relates to the discovery of a novel derivative of amlodipine, the use thereof, and methods of making the same. Specifically, the present invention provides a compound of the following formula (1):

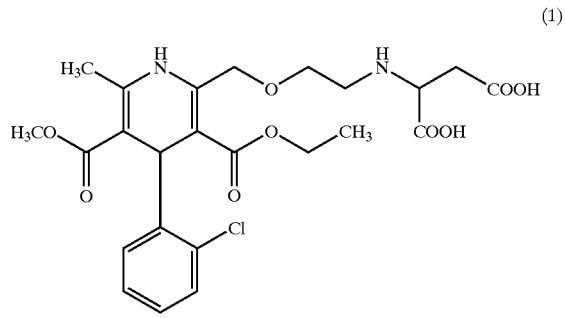

or a pharmaceutically acceptable salt thereof.

The compound of formula (1) is useful as a calcium channel blocker and thus further aspects of the invention relate to a pharmaceutical composition comprising an effective amount of a compound of formula (1) or a pharmaceutically acceptable salt thereof and a pharmaceutically acceptable excipient as well as to a method of treating angina or hypertension by administering to a patient in need thereof an effective amount of a compound of formula (1) or a pharmaceutically acceptable salt thereof. Further, the present invention can be used in combination with amlodipine as a pharmaceutically active ingredient composition.

DETAILED DESCRIPTION OF THE INVENTION

Figure 1:
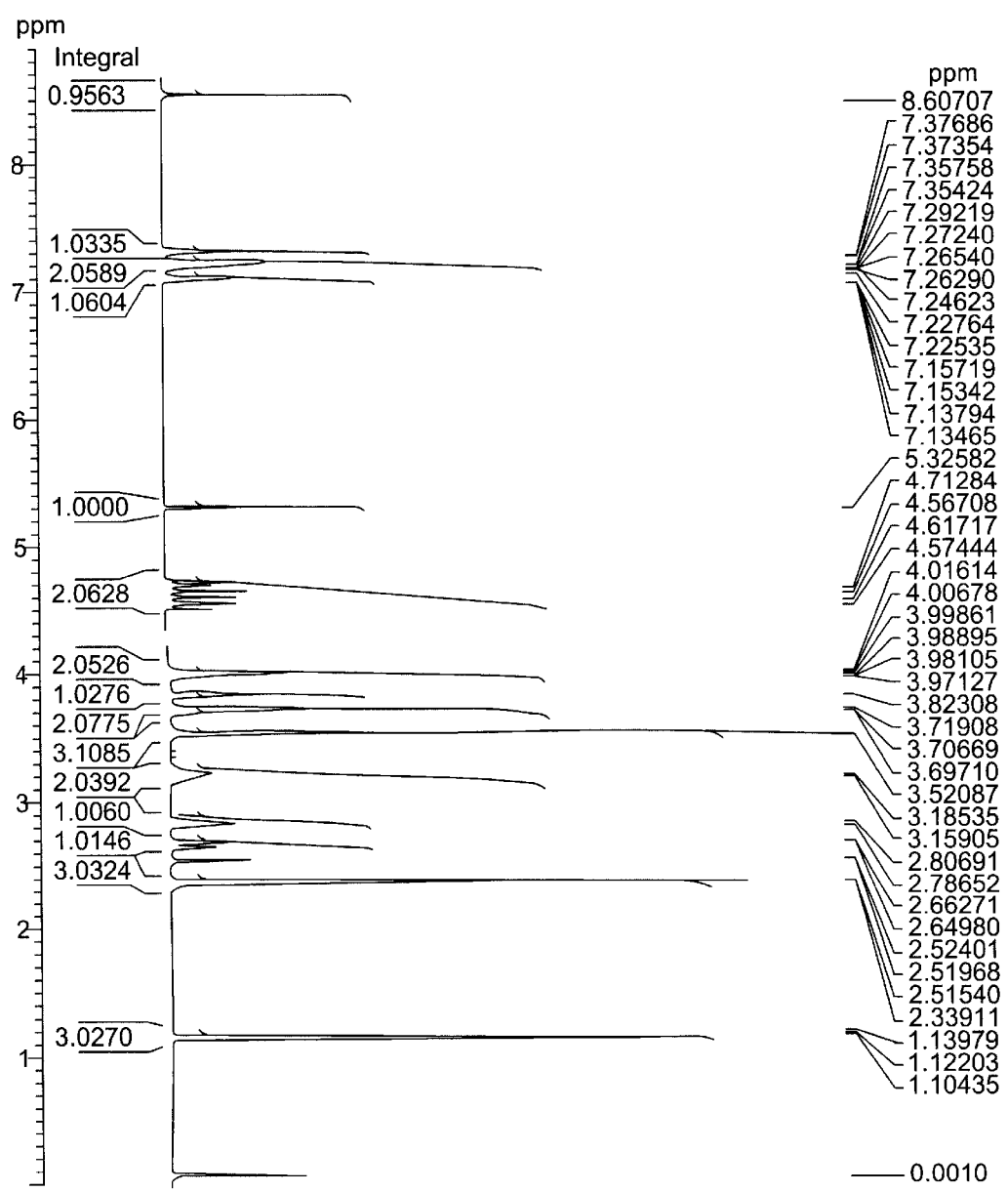
FIG. 1 shows an $^1$H-NMR of the compound produced in Example 1.

The compound of formula (1) can be described as N-(2-{[4-(2-chlorophenyl)-3-(ethoxycarbonyl)-5-(methoxycarbonyl)-6-methyl-1,4-dihydro-2-pyridinyl]methoxy}ethyl)aspartic acid. It is understood that the compound represented by formula (1) may exist as the free acid form or as the corresponding zwitter ion form and that while both forms are included within the meaning of the structural formula, for simplicity sake, only the free acid form is shown. Further, while the compound of formula (1) is referred to in the singular, it should be understood that the compound can exist as one of several enantiomers due to the presence of two chiral centers; one on the 1,4-dihydropyridine ring and another at the amino nitrogen substituent. The individual enantiomers as well as mixtures thereof are all are embraced by the singular "compound."

The compound of formula (1) can be in the form of a salt and is typically a pharmaceutically acceptable salt. Salts include those formed with a metal cation such as an alkali metal cation; those formed with ammonia or an amine compound including mono-, di-, or tri-alkylamine compounds and ring amine compounds; or with an acid. More specifically, metal salts include sodium, potassium and lithium salts of the compound of formula (1). Ammonia and amine salts include salts made with ammonium, methylamine, dimethylamine, triethylamine, pyridine, and amlodipine. Suitable acid salts include inorganic and organic acids such as hydrochloric, sulfuric, phosphoric, acetic, propionic, maleic, fumaric, tartaric, benzoic, methane sulfonic, and benzene sulfonic acid. Salts can also be formed with ambivalent compounds such as aminoacids, e.g. glycine or alanine. The salt of the compound of formula (1) can be a mono-salt, a di-salt, or a mixed salt. Preferred salts include salts made with a pharmaceutically acceptable acid, especially maleic acid.

The compound of formula (1) and its salts are normally solid at room temperature and can be crystalline or amorphous. The crystalline forms include anhydrate forms, hydrated forms and solvate forms. The compound may be isolated and thus of relatively high purity, typically greater than 50 wt % pure, preferably greater than 75 weight % pure, more preferably greater than 90 weight % pure. However, relatively impure forms are also included as are dissolved forms.

The compound of formula (1) can be made by reacting amlodipine or a salt thereof with maleic acid. The reaction is illustrated below.

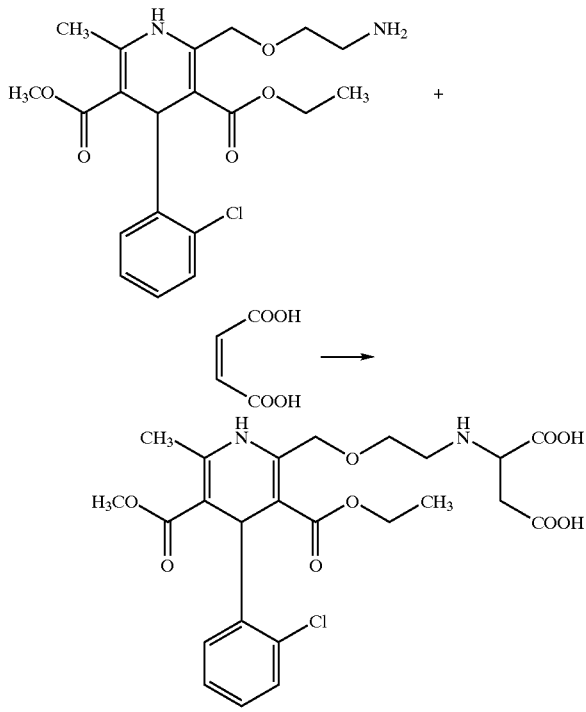

In general, the formation reaction of the compound of formula (1) can be carried out by bringing amlodipine free base or a salt thereof and maleic acid into intimate contact with each other. However, merely contacting amlodipine and maleic acid under mild conditions, such as good conditions for acid addition salt formation, can result in low conversion rates and very low yields; e.g. no formation, due to short contact times. The reaction is essentially a Michael addition and is thus advanced by using conditions of higher pH, higher temperature, and longer reaction or contact time. The reaction is preferably carried out in a melt phase or in a solution. A "melt phase" means that amlodipine is melted at least momentarily while in the presence of maleic acid. When carried out in solution, the temperature is preferably at least 60° C., more preferably at least 80° C., and typically within the range of 85° C. to 110° C. Among solvents suitable for the addition reaction are polar aprotic solvents, for example N,N-dimethylformamide, alcohols such as ethanol and isopropanol, esters such as ethyl acetate, and hydrocarbons such as toluene.

The amlodipine and maleic acid are normally combined in approximately stoichiometric ratios, namely 0.9:1 to 1:0.9.

A convenient method to carry out the reaction is to melt amlodipine maleate. While the maleic acid is in effect pre-combined with the amlodipine, such is specifically contemplated as being within the scope of the present invention. Alternatively, amlodipine free base and amlodipine maleate can be combined in a solvent or dry mixed and melted, etc., to carry out the reaction.

In certain embodiments it is desirable to use excess amlodipine such as in the case where a mixture of amlodipine and a compound of formula (1) is desired. As discussed more fully hereinafter, a large molar excess of amlodipine to maleic acid may be used, e.g. up to 50:1, more typically up to 20:1, and generally 2:1 to 10:1 of amlodipine to maleic acid on a molar basis to form the desired mixture.

Amlodipine free base may be prepared according to the procedures generally outlined in U.S. Pat. No. 4,572,909. Another useful synthesis scheme for making amlodipine or salts thereof in good yields and purity via a phthalimidoamlodipine intermediate is described in commonly-owned provisional application serial No. 60/258,613, filed Dec. 29, 2000, the entire contents of which are incorporated herein by reference, and in commonly-owned co-pending U.S. patent application Ser. No. 09/809,351, filed on Mar. 16, 2001 and entitled "Process for Making Amlodipine, Derivatives Thereof, and Precursors Therefor," the entire contents of which are incorporated herein by reference. Maleic acid is commercially available.

The compound (1) may be isolated from the reaction medium by conventional methods such as evaporation, precipitation, or by extraction and crystallisation. Similarly, the compound of formula (1) can be purified by recrystallization from a solution or hot slurry, for example at reflux temperature in an appropriate solvent, e.g., an ester such as ethyl acetate, an alcohol such as ethanol, propan-2-ol or butan-2-ol, or a ketone such as acetone. The enantiomers may be separated by crystallization or chromatography, optionally in the form of a salt, for example as salt with an optically active base or acid by methods generally known in the art.

Treatment of compound (1) with an equivalent amount of an acid such as maleic acid optionally followed by an isolation step such as precipitation, evaporation or lyophilization, produces an acid addition salt of the compound of formula (1) with the acid. Other salts of compound (1) may be formed by reaction with an equivalent amount of a base, such as for example sodium hydroxide to form a sodium or di-sodium salt of the compound of formula (1).

The compound of formula (1) and its pharmaceutically acceptable salts are useful calcium channel blockers and thus can be used to treat any cardiac condition that would be benefited by administration of a calcium channel blocker.

The calcium channel blocking activity of the compound of the invention (ability to inhibit the movement of calcium into a cell) has been shown by measuring the degree of reduction of contraction of an isolated heart tissue induced by an addition of calcium ions in vitro.

In particular, the compound of formula (1) and its pharmaceutically acceptable salts can be used to treat or prevent hypertension or angina by administering an effective amount to a patient in need thereof. The specific form of angina is not particularly limited and specifically includes chronic stable angina pectoris and vasospastic angina (Prinzmetal's angina). The compound can be administered by any suitable route including orally or parenterally. The "patients" intended to be treated include human and non-human animals especially non-human mammals.

The compound is usually administered as part of a pharmaceutical composition. Accordingly, a further aspect of the invention is a pharmaceutical composition for treating or preventing hypertension or angina that comprises an effective amount of a compound of formula (1) or a pharmaceutically acceptable salt thereof and a pharmaceutically acceptable excipient. Excipients include any inert or non-active material used in making a pharmaceutical dosage form. For example, tablet excipients include, but are not limited to, calcium phosphate, cellulose, starch or lactose. Capsules such as those made of gelatin, may contain or carry the compound of fornmula (1) or a pharmaceutically acceptable salt thereof alone or in admixture with other excipients. Liquid dosage forms are also included such as oral liquids in the form of liquors or suspensions, as well as injectable solutions. The pharmaceutical composition may be formulated for transdermal administration in the form of a patch. All of the above-described pharmaceutical compositions may optionally contain one or more of each of the following excipients: carriers, diluents, colorants, flavoring agents, lubricants, solubilizing agents, disintegrants, binders and preservatives.

The pharmaceutical composition is normally provided in a unit dose. A unit dose is typically administered once or twice daily, more typically once daily. In the case of a transdermal patch, the unit dose (one patch) is generally applied at least once a month, more commonly at least once a bi-week, and typically once a week. An effective amount of the compound of formula (1) or a pharmaceutically acceptable salt thereof in a unit dose for treating or preventing hypertension or angina is generally within the range of 0.1 to 100 mg, typically 1 to 100, more typically 1 to 50 mg, and normally 1 to 20 mg. In solid oral dosage forms (tablets, capsules, etc.), the pharmaceutical composition typically contains about 1, 2.5, 5.0, or 10 mg of the compound of formula (1) or a pharmaceutically acceptable salt thereof. For simplicity, all amounts refer to the corresponding amount of free base provided to the composition.

Another embodiment of the invention relates to the use of a mixture of the compound of formula (1) or a pharmaceutically acceptable salt thereof with amlodipine or a pharmaceutically acceptable salt thereof. The combination of these two pharmaceutically active agents can form a useful pharmaceutically active ingredient composition. Generally, the pharmaceutically active ingredient composition comprises (a) 100 parts by weight of amlodipine or a pharmaceutically acceptable salt thereof and (b) about 0.1 to about 1000 parts by weight, usually 0.5 to 500 parts by weight, more typically 2 to 100 parts by weight of a compound of formula (1) or a pharmaceutically acceptable salt thereof. The amlodipine is preferably in the form of an acid addition salt, especially the maleate salt. The compound of formula (1) is preferably the free base or an acid addition salt, especially the maleate salt. The blend may be obtained directly by controlling the reaction conditions and duration in forming the compound of formula (1); e.g by using elevated temperatures, prolonged contact, proper ratios of maleic acid to amlodipine, etc. Alternatively, the pharmaceutically active ingredient composition can be formed by blending the amlodipine compound with the compound of formula (1) (or their respective salt forms, etc.) in the desired ratio.

The pharmaceutically active ingredient composition can be used in like manner as the compound of formula (1) to form a pharmaceutical composition for treating hypertension or angina. Specifically, such a pharmaceutical composition comprises an effective amount of the pharmaceutically active ingredient composition and a pharmaceutically acceptable excipient as previously described. Similarly the unit dose contains between 0.1 and 100 mg, typically 1 to 100, more typically 1 to 50 mg such as 1 to 20 mg and specifically the solid oral dosage forms (tablets, capsules, etc.) typically contain 1, 2.5, 5.0, or 10 mg of the pharmaceutically active ingredient composition. For simplicity the stated amounts refer to the weight corresponding to the sum of the free base of the amlodipine and the compound of formula (1).

The pharmaceutically active ingredient composition per se or in the form of a pharmaceutical composition can be used to treat or prevent hypertension or angina by administering an effective amount to a patient in need thereof.

All of the pharmaceutical compositions described above can be made by known methods and techniques. For example, the tablets can be made by dry granulation/direct compression or by a classical wet granulation method. Similarly, capsules can be made by blending the ingredients and filling the capsule. A suitable pharmaceutical composition for the above-described pharmaceutically active ingredient composition, having good stability can be obtained by selecting the excipients so as to have a pH of less than 7.0, when measured as a 20 wt % aqueous slurry, as is more fully described in commonly-owned co-pending U.S. patent application Ser. No. 09/809,346, filed on Mar. 16, 2001, now abandoned, and entitled "Pharmaceutical Compositions Comprising Amlodipine Maleate," the entire contents of which are incorporated herein by reference.

Another use of the amlodipine aspartate of formula (1) is as a reference standard or reference marker for evaluating the purity of amlodipine maleate and pharmaceutical compositions comprising amlodipine maleate as is more fully described in commonly-owned U.S. patent application Ser. No. 09/809,347, filed on Mar. 16, 2001, now abandoned, and entitled "Reference Standard For Determining The Purity or Stability of Amlodipine Maleate and Processes Therefor," the entire contents of which are incorporated herein by reference.

The following Examples illustrate the invention.

EXAMPLE 1

16 g of amlodipine and 12 g of amlodipine maleate were melted in a 300 ml flask. The melted substance was cooled to room temperature and dissolved in 300 ml of dichloromethane. The mixture was extracted with 300 ml of a 1M NaOH solution. The organic layer was discarded and the aqueous layer acidified with 55 ml of a 6 M HCl solution. The mixture was extracted with 300 ml of dichloromethane. The layers were separated and the organic layer dried over $Na_2SO_4$. The mixture was evaporated to dryness and the resulting waxy solid recrystallized from ethanol. The obtained sticky solid was dried in a vacuum oven at 40° C. leaving 4.7 g of an off white product.

Yield: 4.7 g (39%)

Mp: 178° C.–183° C. (decomposed)

Purity: greater than 90%

¹H-NMR spectrum:

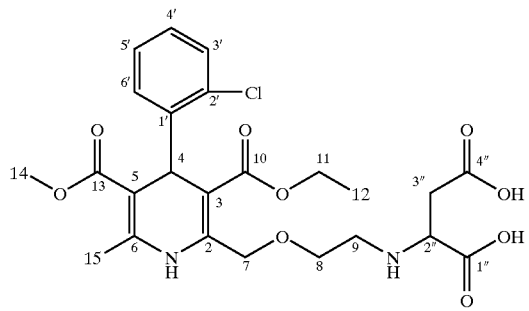

The ¹H-NMR spectrum was measured at 303.2 K on a Bruker Avance-400 in deuterated dimethylsulfoxide at 400 MHz. It is represented on FIG. 1.

| δ | assignment |
|---|---|
| 1.12 | (t, 3H, $J_{11,12}$ = 7.0 Hz, 3xH-12); |
| 2.36 | (s, 3H, 3xH-15); |
| 2.87 | (m, ~2H, 2xH-3"); |
| 3.24 | (m, ~2H, 2xH-9); |
| 3.52 | (s, ~3H, 3xH-14); |
| 3.76 | (bs, 2H, 2xH-8); |
| 4.00 | (m, 3H, 2xH-11 + H-2"); |
| 4.65 | (m, 2H, 2xH-7); |
| 5.33 | (s, 1H, H-4); |
| 7.13 | (dt, 1H, $J_{3',4'}$ = $J_{4',5'}$ = 7.6 Hz, $J_{4',6'}$ = 1.8 Hz, H-4'); |
| 7.26 | (m, 2H, H-3' + H-5'); |
| 7.37 | (d, 1H, $J_{5',6'}$ = 7.8 Hz, H-6'); |
| 8.61 | (s, 1H, NH). |

Figure 2:
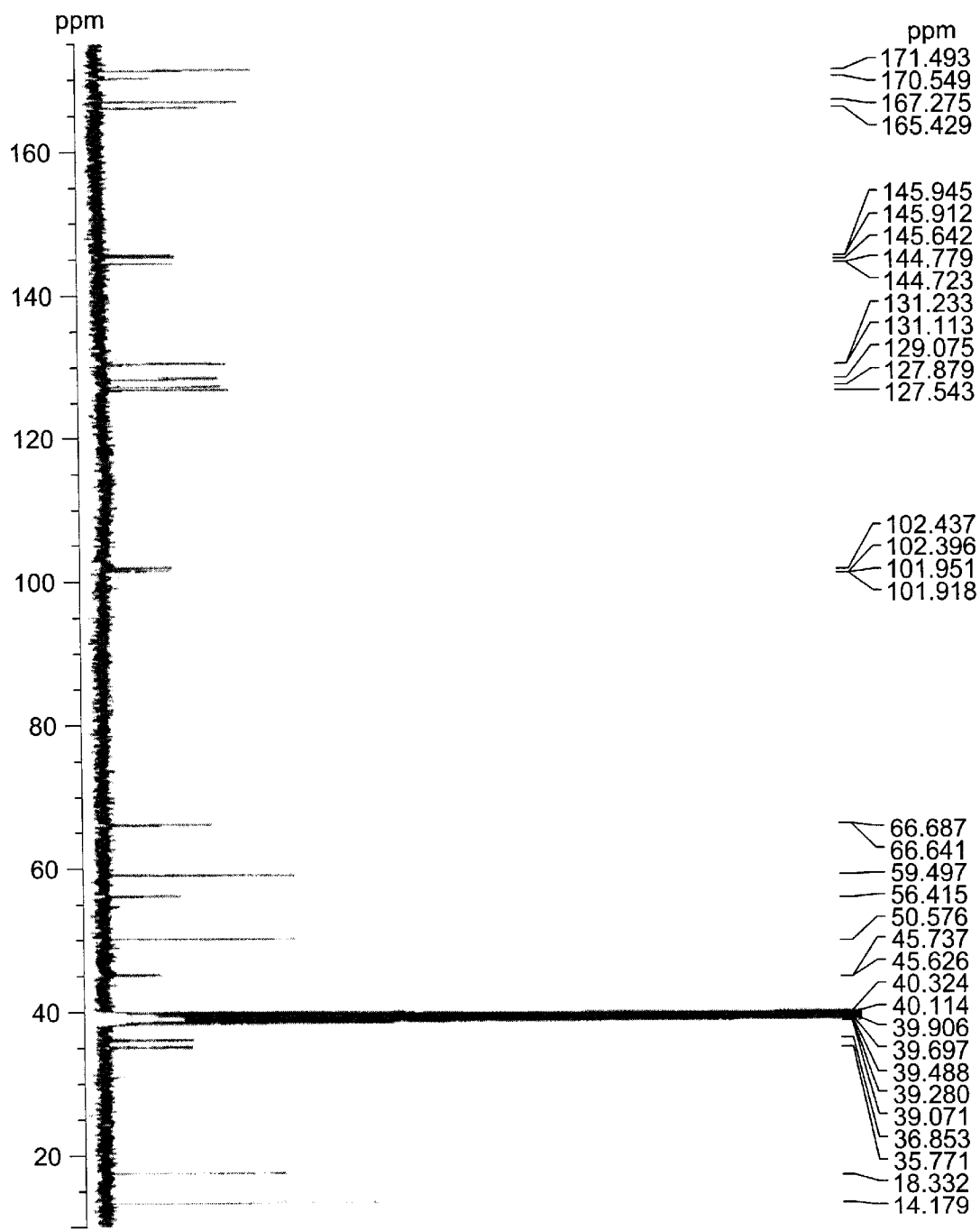
FIG. 2 shows a $^{13}$C-NMR of the compound produced in Example 1.

¹³C-NMR spectrum:
The ¹³C-NMR spectrum was measured at 303.2 K on a Bruker Avance-400 in deuterated dimethylsulfoxide at 100.6 MHz. It is represented on FIG. 2.

| δ | assignment |
|---|---|
| 14.18 | (C-12); |
| 18.33 | (C-15); |
| 35.77 | (C-3"); |
| 36.85 | (C-4); |
| 45.63, 45.74 | (C-9); |
| 50.58 | (C-14); |
| 56.42 | (C-2"); |
| 59.50 | (C-11); |
| 66.64, 66.69 | (C-7, C-8); |
| 101.92, 102.40 | (C-3, C-5); |
| 127.54 | (C-5'); |
| 127.88 | (C-4'); |
| 129.07 | (C-2'); |
| 131.11 | (C-6'); |
| 166.43 | (C-10); |
| 167.28 | (C-13); |

EXAMPLE 2

A mixture of amlodipine maleate and the compound of formula (1)

2.00 g of Amlodipine maleate was dissolved in 80 ml 2-propanol at 92° C. The clear slightly yellow coloured solution was refluxed during 10 minutes and subsequently allowed to cool to ambient temperature without stirring. A solid was formed and the suspension was allowed to cool to 4° C. The solid was filtered off and washed with 5 ml cold 2-propanol and dried under vacuum at ambient temperature for 1 hour.

Yield: 1.86 g of a mixture comprising 1% of the compound of formula (1) and 99% of amlodipine maleate.

EXAMPLE 3

Pharmaceutical Compositions (tablets) containing the compound of Formula (1)

|  | per 5 mg tablet | per 10 mg tablet |
|---|---|---|
| Compound of formula (1) (Amlodipine aspartate) | 5.0 mg | 10.0 mg |
| Calcium hydrogen phosphate anhydrous | 63.0 mg | 126.0 mg |
| Magnesium oxide | 4.0 mg | 8.0 mg |
| Microcrystalline cellulose | 126.0 mg | 252.0 mg |
| Sodium starch glycollate | 4.0 mg | 8.0 mg |
| Magnesium stearate | 2.0 mg | 4.0 mg |
| Total | 204.0 mg | 408.0 mg |

Manufacturing Process

The amlodipine aspartate is sieved through a 500 μm screen.

The calcium hydrogenphosphate anhydrous, magnesium oxide, microcrystalline cellulose, sodium starch glycollate and magnesium stearate are sieved through a 850 μm screen.

The amlodipine aspartate, magnesium oxide and about 30% of the amount of microcrystalline cellulose (MCC) are mixed in a free fall mixer for 10 minutes at about 25 rpm.

The remaining amount of MCC, calcium hydrogenphopsphate anhydrous and sodium starch glycollate are added and the blend is mixed for 15 minutes at about 25 rpm.

Magnesium stearate is added and the powder blend is mixed for another 5 minutes at about 25 rpm.

Amlodipine aspartate tablets are compressed.

EXAMPLE 4

Pharmaceutical Compositions (tablets) containing the compound of Formula (1)

|  | per 5 mg tablet | per 10 mg tablet |
|---|---|---|
| Compound of Formula (1) (Amlodipine aspartate) | 5.0 mg | 10.0 mg |
| Calcium hydrogen phosphate anhydrous | 63.0 mg | 126.0 mg |
| Microcrystalline cellulose | 126.0 mg | 252.0 mg |
| Sodium starch glycollate | 4.0 mg | 8.0 mg |
| Magnesium stearate | 2.0 mg | 4.0 mg |
| Total | 200.0 mg | 400.0 mg |

Manufacturing Process

The Amlodipine aspartate is sieved through a 500 μm screen.

The calcium hydrogenphosphate anhydrous, magnesium oxide, microcrystalline cellulose, sodium starch glycollate and magnesium stearate are sieved through a 850 μm screen.

The Amlodipine aspartate, microcrystalline cellulose, calcium hydrogenphopsphate anhydrous and sodium starch glycollate are transferred into a free fall mixer and the blend is mixed for 15 minutes at about 25 rpm.

Magnesium stearate is added and the powder blend is mixed for another 5 minutes at about 25 rpm.

Amlodipine aspartate tablets are compressed.

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A compound of formula (1)

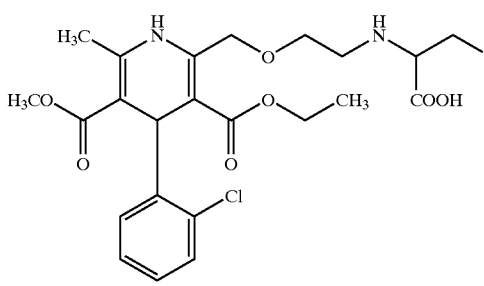

(1)

or a pharmaceutically acceptable salt thereof.

2. The compound according to claim 1, wherein said compound is an alkali metal salt, an amine salt or an acid addition salt.

3. The compound according to claim 2, wherein said compound is an amine salt.

4. The compound according to claim 3, wherein said amine salt is an amlodipine salt of said compound.

5. The compound according to claim 2, wherein said compound is a maleate salt.

6. A pharmaceutical composition for treating angina or hypertension comprising an effective amount of a compound of formula (1)

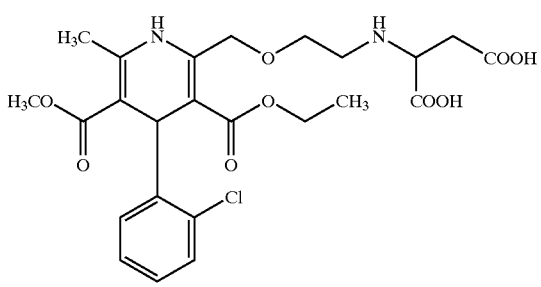

(1)

or a pharmaceutically acceptable salt thereof and a pharmaceutically acceptable excipient.

7. The pharmaceutical composition according to claim 6, wherein said compound of formula (1) is in a pharmaceutically acceptable salt form and said composition is in a unit dose form.

8. The pharmaceutical composition according to claim 7, wherein said pharmaceutically acceptable salt is a maleate salt and said compound of formula (1) is contained in an amount corresponding to 0.1 to 100 mg.

9. The pharmaceutical composition according to claim 6, wherein said composition is in a unit dose form and said compound of formula (1) is contained in an amount corresponding to 1.0 to 100 mg.

10. A process, which comprises: reacting amlodipine or a salt thereof with maleic acid to form a compound of formula (1) or a salt thereof:

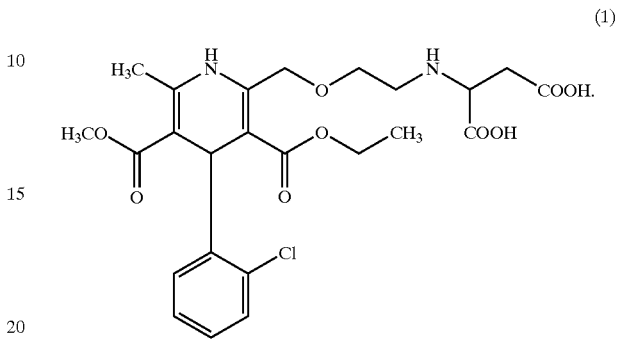

(1)

11. The process according to claim 10, wherein said reacting step is carried out at a temperature greater than 60° C.

12. The process according to claim 10, wherein said reacting step is carried out in a melt phase.

13. The process according to claim 12, wherein said reacting step is carried out at a pH of greater than 7.

14. The process according to claim 10, wherein said reacting step is carried out in a solvent.

15. A process for treating or preventing angina or hypertension which comprises administering an effective amount of the compound according to claim 1 to a patient in need thereof.

16. A pharmaceutically active ingredient composition comprising a mixture of amlodipine or a pharmaceutically acceptable salt thereof and a compound of formula (1)

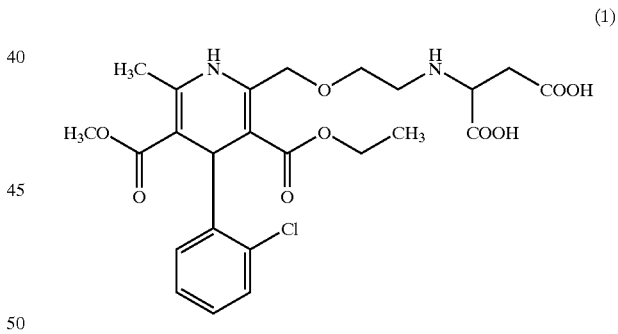

(1)

or a pharmaceutically acceptable salt thereof.

17. The composition according to claim 16, wherein said composition comprises 100 parts by weight of said amlodipine and 0.1 to 1000 parts by weight of said compound of formula (1).

18. The composition according to claim 17, wherein said composition comprises said compound of formula (1) in an amount of 0.5 to 500 parts by weight.

19. The composition according to claim 18, wherein said composition comprises 100 parts of amlodipine maleate and 2 to 100 parts of said compound of formula (1) or the maleate salt thereof.

20. A pharmaceutical composition for treating or preventing angina or hypertension comprising an effective amount of the pharmaceutically active ingredient composition according to claim 16 and a pharmaceutically acceptable excipient.

21. The pharmaceutical composition according to claim 20, wherein said pharmaceutical composition is a unit dose form.

22. The pharmaceutical composition according to claim 21, wherein said effective amount of said pharmaceutically active ingredient composition is within the range of 1 to 20 mg.

23. A process for treating or preventing angina or hypertension which comprises administering to a patient in need thereof an effective amount of a pharmaceutically active ingredient composition according to claim 16.

* * * * *